United States Patent [19]

Haber et al.

[11] Patent Number: 5,524,613
[45] Date of Patent: Jun. 11, 1996

[54] CONTROLLED MULTI-PHARMACEUTICAL INHALER

[75] Inventors: Terry M. Haber, Lake Forest; William H. Smedley, Lake Elsinor; Clark B. Foster, Laguna Niguel, all of Calif.

[73] Assignee: Habley Medical Technology Corporation, Laguna Hills, Calif.

[21] Appl. No.: 126,991

[22] Filed: Sep. 24, 1993

Related U.S. Application Data

[63] Continuation-in-part of Ser. No. 111,614, Aug. 25, 1993.

[51] Int. Cl.⁶ .................................................. A61M 15/00
[52] U.S. Cl. ............................... 128/203.15; 128/203.12
[58] Field of Search .......................... 128/200.23, 203.15, 128/203.12, 203.18, 203.23, 203.21, 200.14, 203.24, 200.21, 200.24

[56] References Cited

U.S. PATENT DOCUMENTS

| | | | |
|---|---|---|---|
| 3,155,573 | 11/1964 | Fowler | 424/40 |
| 3,518,992 | 7/1967 | Altounyan et al. | 128/203.21 |
| 3,888,252 | 6/1975 | Side et al. | 128/203.15 |
| 3,888,253 | 6/1975 | Watt et al. | 128/203.15 |
| 3,971,377 | 7/1976 | Damani | 128/200.17 |
| 4,116,195 | 9/1978 | James | 604/244 |
| 4,117,844 | 10/1978 | James | 128/203.15 |
| 4,338,931 | 7/1982 | Cavazza | 128/203.15 |
| 4,811,731 | 3/1989 | Newell et al. | 128/203.15 |
| 4,841,964 | 6/1989 | Hurka et al. | 128/203.15 |
| 5,002,048 | 3/1991 | Makiej, Jr. | 128/200.23 |
| 5,046,493 | 9/1991 | Kropkowski et al. | 128/203.15 |
| 5,048,514 | 9/1991 | Ramella | 128/203.21 |
| 5,184,761 | 2/1993 | Lee | 222/402.2 |
| 5,201,308 | 4/1993 | Newhouse | 128/203.15 |
| 5,217,004 | 6/1993 | Blasnik et al. | 128/203.23 |
| 5,224,472 | 6/1993 | Pesenti et al. | 128/200.23 |
| 5,239,992 | 8/1993 | Bougamont et al. | 128/203.15 |
| 5,239,993 | 8/1993 | Evans | 128/203.15 |
| 5,287,850 | 2/1994 | Haber et al. | 128/203.21 |

FOREIGN PATENT DOCUMENTS

| | | | |
|---|---|---|---|
| 628931 | 10/1978 | U.S.S.R. | 128/203.15 |
| 1577796 | 7/1990 | U.S.S.R. | 128/203.15 |
| 1591990 | 9/1990 | U.S.S.R. | 128/203.15 |
| 2165159 | 4/1986 | United Kingdom | 128/203.15 |
| WO90/07351 | 7/1990 | WIPO . | |
| 9218188 | 10/1992 | WIPO | 128/203.15 |

OTHER PUBLICATIONS

M Spinhaler® Turbo-Inhaler instruction leaflet, Fisons Corporation.

*Primary Examiner*—Aaron J. Lewis
*Attorney, Agent, or Firm*—Townsend and Townsend and Crew

[57] ABSTRACT

A powdered pharmaceutical inhaler (2) includes a source of pressurized gas (4), a pharmaceutical transfer assembly (104) and a mouthpiece assembly (106). The pharmaceutical transfer assembly includes a pharmaceutical reservoir (172, 174) containing undivided supplies of at least one pharmaceutical (173, 175). Quantities of the pharmaceutical are transferred from the pharmaceutical reservoir to an entrainment region along a flow path (188) through the inhaler by one or more dosing members (120–128). By using multiple reservoirs with different pharmaceuticals, a variable dose can be simultaneously inhaled in a single application. An auxiliary ambient air flow path (238) can be used to surround the pressurized gas flow path at the exit of the inhaler. A view port (184) can be used to visually inspect the entrainment region for the presence and amount of pharmaceutical to be inhaled. A preferred embodiment pocket sized and streamlined embodiment includes air compression for assisted inhalation combined with dosing member loading. In the streamlined embodiment, after air compression, an air valve activated by inhalation entrains powered medication in the dosing members for inhalation and consequent dispensing of the prescriptive dosage to the patient.

28 Claims, 16 Drawing Sheets

1

CONTROLLED MULTI-PHARMACEUTICAL INHALER

CROSS-REFERENCE TO RELATED APPLICATIONS

This invention is related to U.S. patent application Ser. No. 07/747,375 filed Aug. 20, 1991 for TIMING AND VELOCITY CONTROLLED POWDERED PHARMACEUTICAL INHALER, now U.S. Pat. No. 5,287,750, issued Feb. 22, 1994, the disclosure of which is incorporated by reference.

Additionally, this application is a continuation-in part of application Ser. No. 08/111,614 filed Aug. 25, 1993 entitled CONTROLLED MULTI-PHARMACEUTICAL INHALER, now pending, and having the inventors herein.

BACKGROUND OF THE INVENTION

Certain pharmaceuticals can be administered in powdered form through inhalation of the powdered pharmaceutical down into the lungs. This type of pulmonary pharmaceutical delivery has several advantages. It eliminates the requirement for the use of needles and syringes, which many patients are uncomfortable with. Also, certain pharmaceuticals have a relatively short shelf life when in liquid form. Therefore, administration in powdered form may eliminate the necessity to reconstitute the pharmaceutical with a liquid diluent.

Although not all pharmaceutical products are suitable for being administered in powdered form, many pharmaceuticals have been formulated for pulmonary inhalation. For example, Novo Nordisk of Bagsvaerd, Denmark, sells a nasal insulin preparation which is inhaled by the user. Other types of pharmaceuticals are administered in powdered form as well. Another pharmaceutical for oral inhalation by asthmatic patients is sold by Glaxo of Bern, Switzerland. The medication is delivered by a device, sold as the DISKHALER®, which has a rotatable disk with a number of regions containing pharmaceutical crystals. The disk is rotated to a position which brings one of the pharmaceutical-containing packets in line with a needle cannula; the needle cannula is then manipulated to puncture the packet to allow the pharmaceutical to be inhaled. Another type of powdered pharmaceutical delivery device is sold by Fisons Corporation of Bedford, Mass., under the trademark SpinHaler®. It uses a gelatin capsule containing the powdered pharmaceutical. The capsule is pierced by a needle which allows the pharmaceutical to be pulmonarily inhaled through the mouth and into the lungs.

One of the problems with prior art powdered pharmaceutical delivery devices is that the device is reused, as is normal for non-single user devices. The powdered pharmaceutical often clings to, coats or even cakes onto various surfaces of the device especially those in direct contact with the air stream surface of the device. These surfaces, which often have been moistened by the user's breath, can become distorted and contaminated; the contaminated surfaces may create additional health problems during subsequent use due to the proliferation of bacterial contamination.

Another problem with prior art powdered pharmaceutical delivery devices relates to the inability of physician and/or user to selectively vary the dose. That is, with conventional inhalers the dose is typically fixed so that, for example, the entire contents of a single capsule is administered to the user with each use. Also, conventional pharmaceutical inhalers are not typically constructed for the simultaneous intermixing and inhalation of two or more pharmaceutical components.

Finally, prior art powdered pharmaceutical inhalation devices are not able to accurately dose powdered pharmaceuticals in doses of less than 500 microgram volumes.

SUMMARY OF THE INVENTION

This invention is directed to a pharmaceutical inhaler which provides the user with a great amount of flexibility in determining the amount of pharmaceutical to be inhaled and permits the user to select a mixture of two or more pharmaceuticals to be administered simultaneously as a single dose.

The powdered pharmaceutical inhaler includes a source of gas, preferably pressurized gas, a pharmaceutical transfer assembly and a mouthpiece assembly. The pharmaceutical transfer assembly includes a pharmaceutical reservoir containing an undivided supply of a pharmaceutical. Quantities of the pharmaceutical are transferred from the pharmaceutical reservoir to an entrainment region along a gas flow path through the inhaler by one or more dosing members. By using two or more reservoirs containing different pharmaceutical products, a variably-proportioned dose of two or more pharmaceuticals can be inhaled in a single application. An auxiliary or secondary gas flow path can be used to surround the gas flow path at the exit of the inhaler. A magnifying viewing window can be used to visually inspect the presence, amount and after inhalation, the absence of additional pharmaceutical to be inhaled.

One of the primary advantages of the invention is the flexibility it provides the user as to the type, quantity and relative proportions of the pharmaceuticals to be administered simultaneously as a single dose. Using the visualization lens permits the user to determine the presence of the pharmaceutical to be inhaled. Making the dosing members of a contrasting color to the pharmaceutical to be inhaled makes this visualization quite effective and usable as a "dose-delivered" indicator as well. Use of a pressurized gas to fluidize and suspend the pharmaceutical provides aural and tactile feedback to the user to provide an indication that the medication has been properly fluidized, suspended and inhaled.

Another advantage of the invention is its ability to be used with much smaller doses than prior art inhalers. The invention makes possible the accurate delivery of doses of 50, 100, 250 and 500 microgram volumes of two or more different pharmaceutical products fluidized within the same air stream and having a timed breath assist boosting feature for the pharmaceutical products.

The invention can also provide for a coaxial airstream consisting of a generally low pressure, high volume outer airstream created by the user's act of inhaling. The use of a pressurized air source is especially useful whenever a powdered pharmaceutical is moderately or very difficult to deagregate, fluidize and suspend in an airstream. If desired, the quantity and/or pressure of the air delivered from the pressurized air source could be varied according to the partial size, specific gravity and the type of the pharmaceutical(s) as well as the particular pulmonary capacity and efficiency and other physiological characteristics of the user.

A preferred and compact embodiment of the device includes a rounded pocket size embodiment in which air compression for assisted inhalation combines with dosing member loading. Thereafter, and after air compression, an air valve activated by inhalation entrains powered medication in the dosing members for inhalation and consequent dispensing of the prescriptive dosage to the patient.

Other features and advantages of the invention will appear from the following description in which the preferred embodiments have been set forth in detail in conjunction with the accompanying drawings.

DESCRIPTION OF THE PREFERRED EMBODIMENTS

Figure 1:
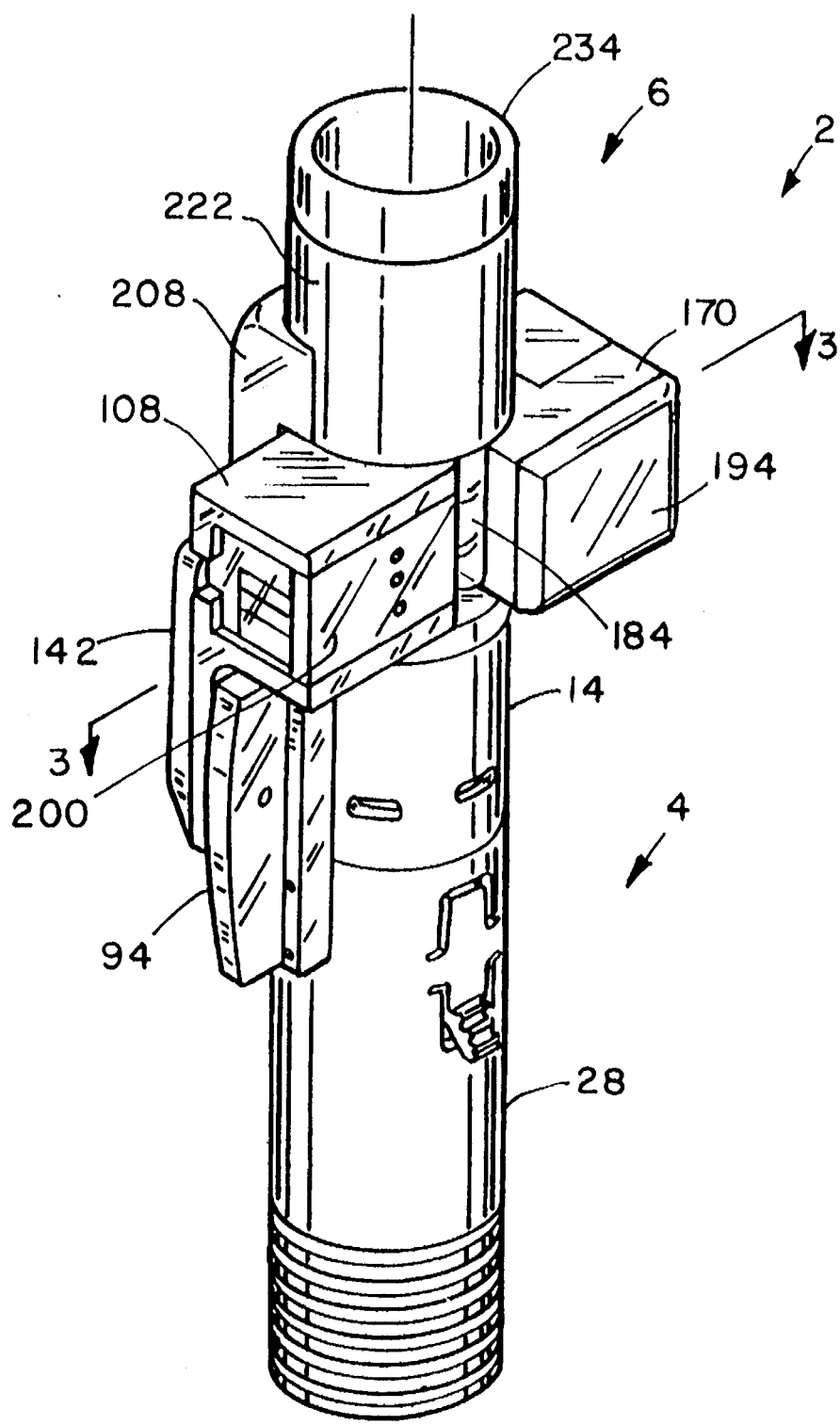
FIG. 1 is an isometric view of the pharmaceutical inhaler made according to the invention.
Figure 2:
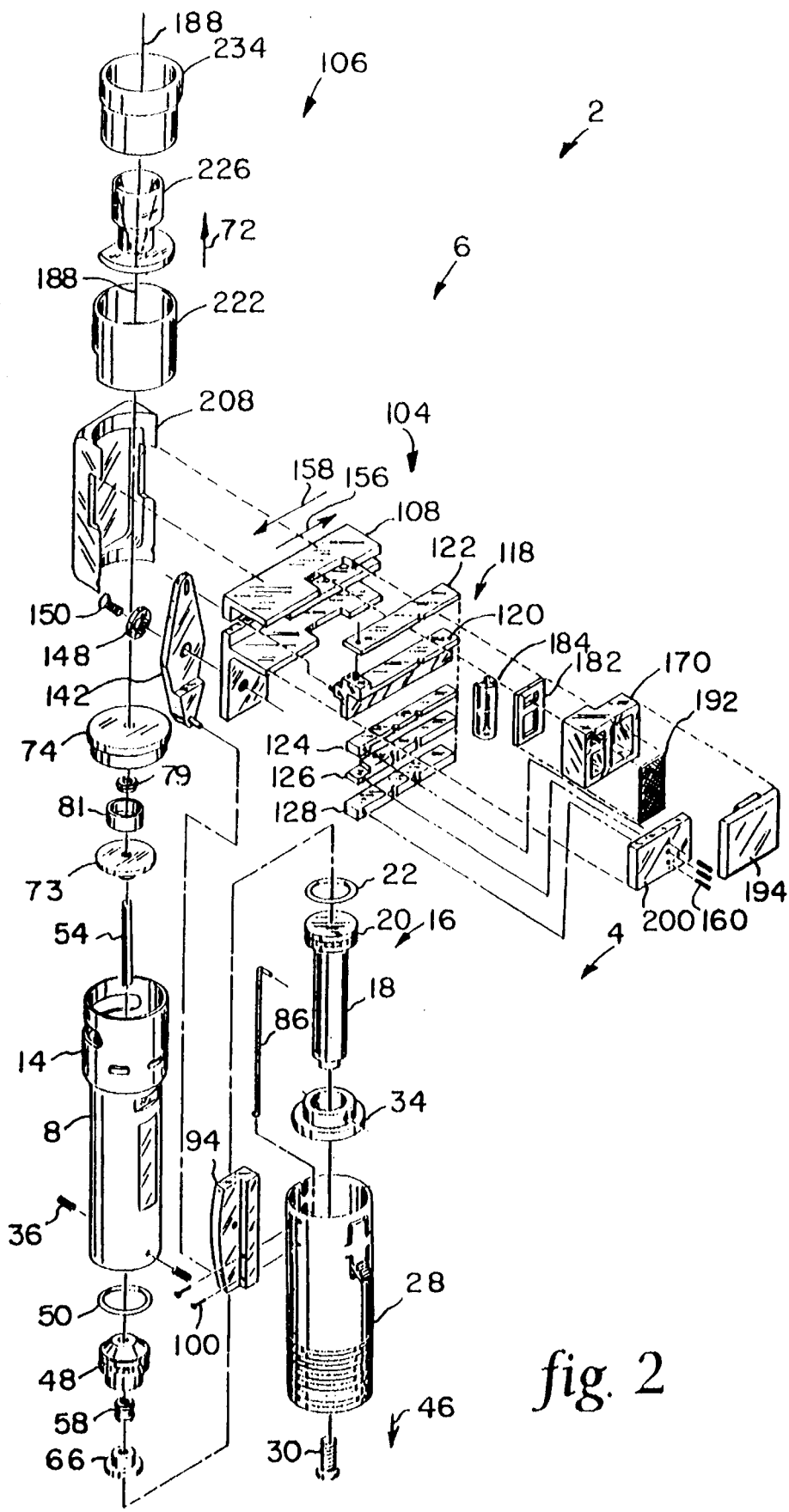
FIG. 2 is an exploded isometric view of the parts of the inhaler of FIG. 1.
Figure 2A:
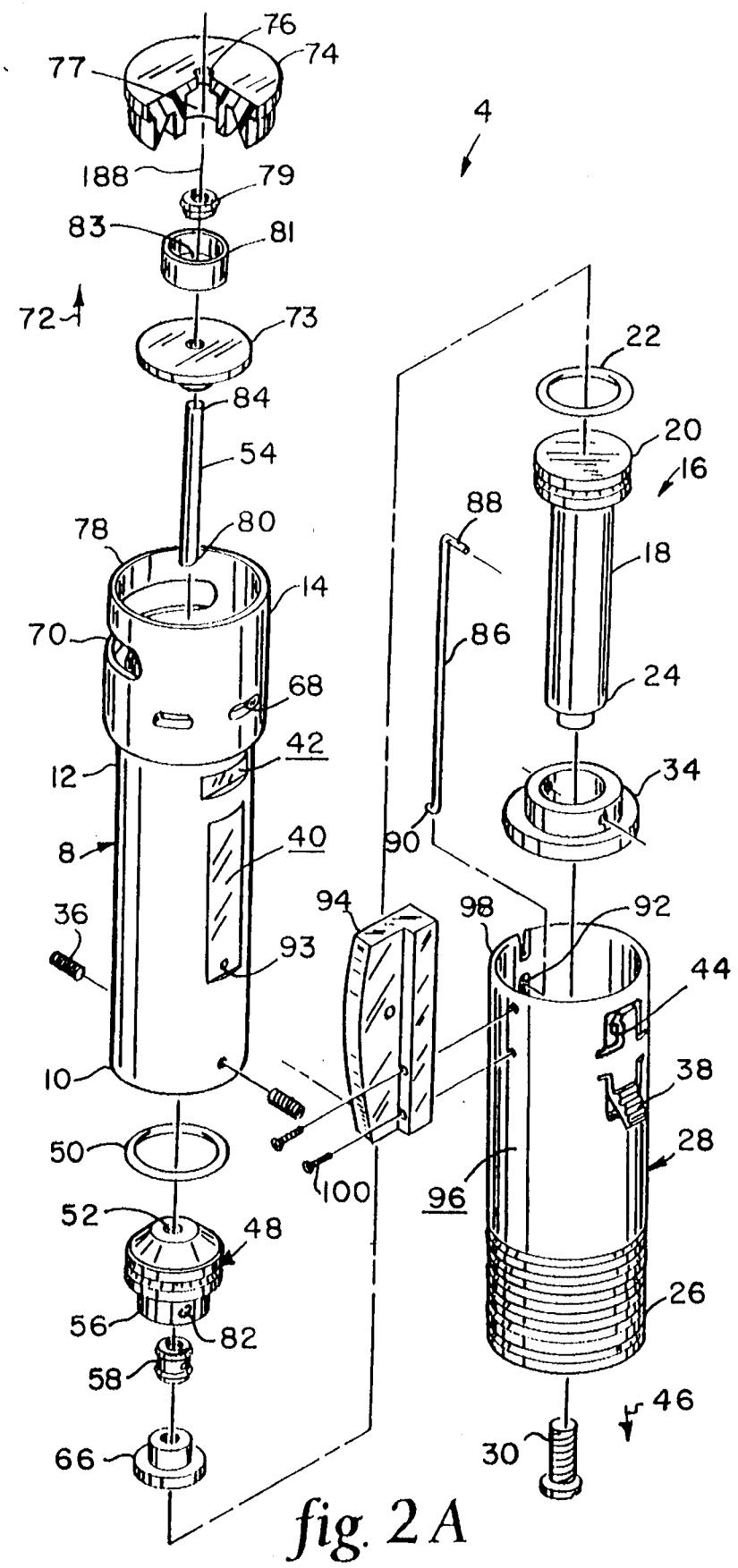
FIGS. 2A and 2B are enlarged views of the components of FIG. 2 constituting the pressurized gas source assembly and the inhaler subassembly, respectively.
Figure 2B:
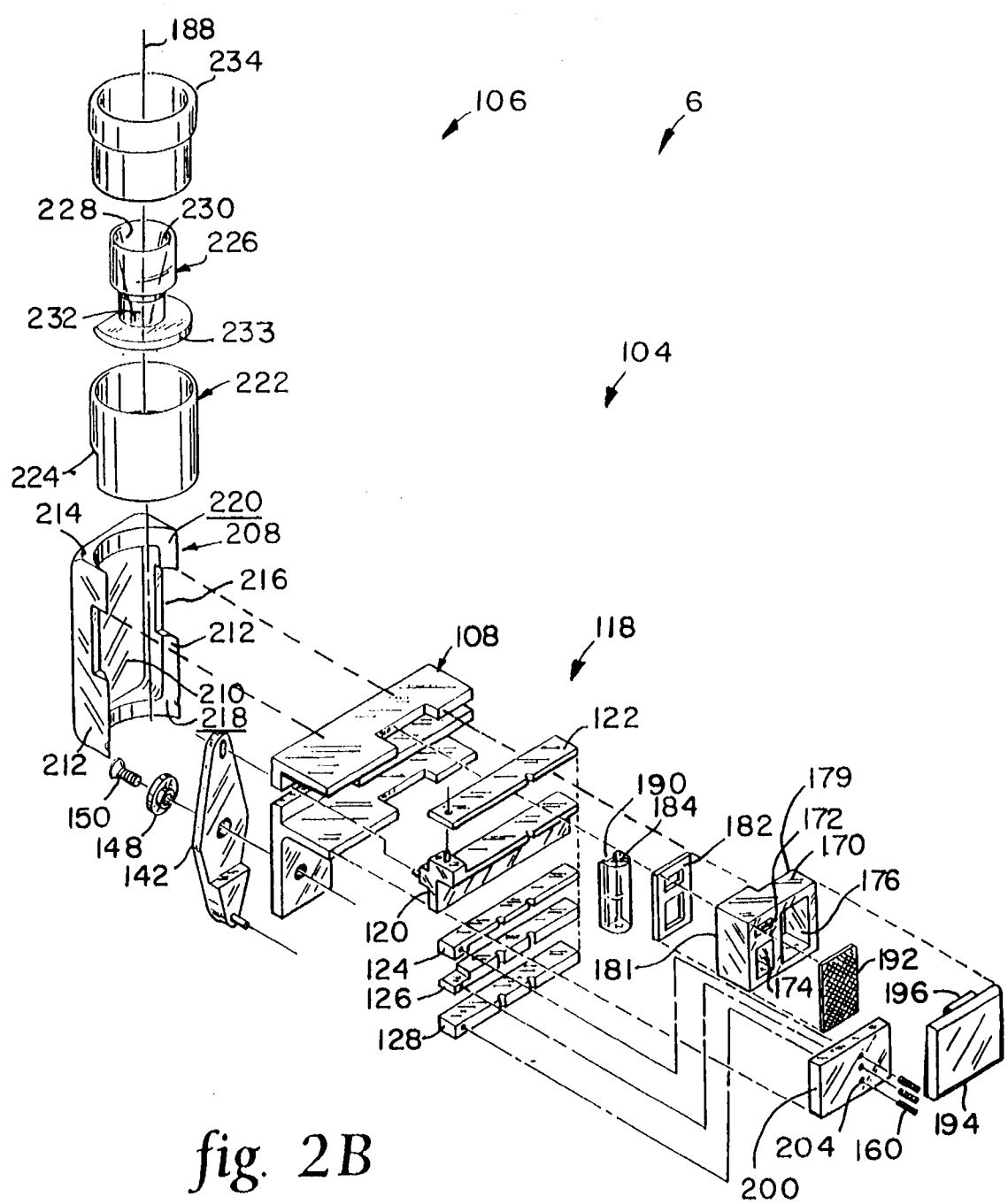
Figure 3:
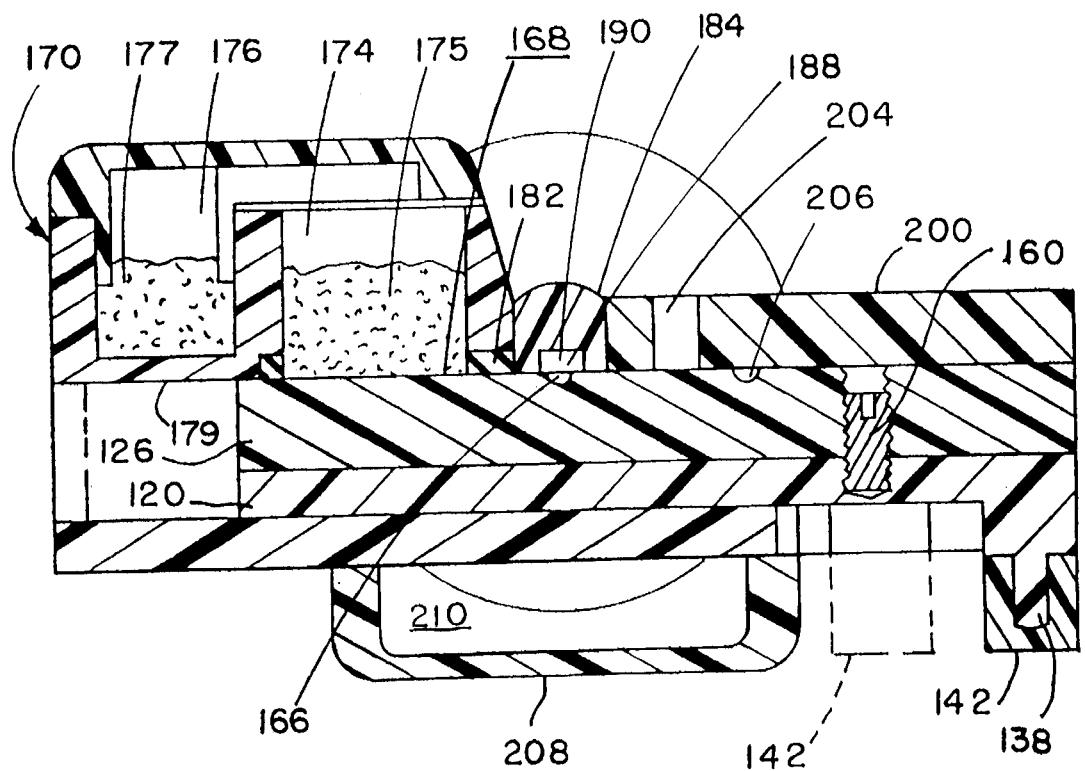
FIG. 3 is a cross-sectional view taken along line 3—3 of FIG. 1.

FIGS. 1–3 illustrate the pharmaceutical inhaler made according to the invention. Inhaler 2 includes broadly a pressurized gas source assembly 4, shown best in FIG. 2A, and an inhaler subassembly 6, shown best in FIG. 2B.

Assembly 4 includes a cylinder 8 having an open distal end 10 and an open proximal end 12, from which an enlarged cylindrical member 14 extends. The plunger 16 is mounted within cylinder 8 for reciprocal movement therein. Plunger 16 includes a stem 18 and a piston 20. Piston 20 includes an o-ring 22 which provides a seal within the interior of cylinder 8. The distal end 24 of stem 18 is secured to the externally ribbed distal end 26 of a stem handle sleeve 28. Distal end 26 is closed except for a small hole through which a screw 30 passes to engage distal end 24 of stem 18. Thus, driving stem handle sleeve 28 along axis 32 causes plunger 16 to reciprocate within cylinder 8 since stem handle sleeve 28 is large enough to circumscribe cylinder 8.

A stem stop 34 is secured to the distal end 10 of cylinder 8 by a pair of set screws 36. Stem stop 32 prevents the complete removal of plunger 16 from within cylinder 8. Stem handle sleeve 28 includes a finger lever 38. Cylinder 8 includes flattened surfaces 40, 42 which are positioned to underlie finger lever 38. Finger lever 38 controls a catch 44 which rides along surfaces 40, 42. Catch 44 is configured so that when the catch engages surface 42, that is with plunger 16 fully housed within cylinder 8 for maximum pressurization, catch 44 prevents movement of plunger 16 in distal direction 46.

Proximal end 12 of cylinder 8 is normally sealed by a barrel plug 48 which is friction fit within cylinder 8 and provides a good seal against the interior of the cylinder using an o-ring 50. Barrel plug 48 is hollow and has a relatively small proximal opening 52 through which a hollow boost air tube 54 passes. The distal end of 56 of barrel plug 48 has an enlarged counter-bore sized to accept a double-lip seal 58, seal 58 shown best in FIG. 2D. Seal 58 includes a pair of lip seals 60 which engage the interior of barrel plug 48. Double-lip seal 58 is also hollow and includes a pair of interior seals 62, only one of which is shown in FIG. 2D, located at either end of seal 58.

Seal 58 also includes a radial bore 64 which opens into the interior of double-lip seal 58 between interior seals 62. Interior seals 62 are sized to provide the necessary seals against the exterior of boost air tube 54. Boost air tube 54 normally passes through double-lip seal 58 so to be engaged by both interior seals 62. Double-lip seal 58 is held in place by a cap 66 that is secured to distal end 56 of barrel plug 48 using a press fit, an adhesive or other suitable means.

Enlarged cylindrical member 14 includes four ambient air inlets 68 on one side of member 14 and a elongate passageway 70 on the other side of member 14. Inlet 68 and passageway 70 are separated axially with passageway 70 located in a proximal direction 72 relative to air inlet 68. A breath-actuated trigger disk 73, having a diameter smaller than the interior diameter of member 14, is mounted to boost air tube 54 and is positioned to lie between ambient air inlet 68 and passageway 70. An adapter cap 74, having a central bore 76, covers the proximal end 78 of member 14. A single lip seal 79 is mounted within a cavity 77 formed in adapter cap 74, see FIG. 2A, and provides a seal between seal 79 and the outer surface of boost air tube 54 and between seal 79 and adapter cap 74. Seal 79 is held in place by a cup 81 having a hole (not shown) in its bottom 83 through which tube 54 passes. Boost air tube 54 is supported at its ends by barrel plug 48 and adapter cap 74.

As will be discussed below, breath-actuated trigger disk 73 can be moved in proximal direction 72 by inhaling on inhaler subassembly 6; this pulls ambient air through ambient air inlets 68, past breath trigger disk 73 and out passage 70 causing breath trigger disk 73 to move in proximal direction 72. This causes distal end 80 of boost air tube 54 to move in proximal direction 72 and thus be positioned between interior seals 62 at either end of double-lip seal 58. When this occurs, pressurized air within cylinder 8 can pass through a vent hole 82 formed in barrel plug 48, through radial bore 64, through the open distal end 80 of hollow boost air tube 54 and through the open proximal end 84 of tube 54.

Assembly 4 also includes a reset wire form 86 having a radially inwardly angled proximal end 88 and a radially outwardly angled distal end 90. Wire form 86 is used to reset breath trigger disk 73 and boost air tube 54. That is, in the preferred embodiment stem handle sleeve 28 moves approximately 3.5 cm in proximal and distal directions 72, 46. Sleeve 28 has an axially extending slot 92 which is 3 cm long. Distal end 90 engages slot 92 and freely travels within slot 92 throughout most of the axial travel of stem handle sleeve 28. However, the last 0.5 cm movement of sleeve 28 in distal direction 46 causes distal end 90 of wire form 86 to engage the proximal end of slot 92 so to pull reset wire form 86 in distal direction 46 about 0.5 mm. During this movement, proximal end 88 of reset wire form 86 engages breath trigger disk 73 and pulls trigger disk 73 and boost air tube 74 in distal direction 76. This forces distal end 80 of tube 54 past the distal-most seal 62 of double-lip seal 58 thus sealing the interior of cylinder 8 from the interior of boost air tube 54.

A vent hole 93 is formed in cylinder 8 to allow ambient air to enter cylinder 8 when plunger 16 is pulled fully in distal direction 46. This relieves the partial vacuum created during the final distal movement of plunger 16 after end 80 passes the distal-most seal 62.

A cam plate 94 is mounted to the outer surface 96 of sleeve 28 at the proximal end 98 of the sleeve by a pair of screws 100. Cam plate 94 has a cam slot 102 as shown in FIG. 2F. The use of cam slot 102 will be discussed below.

Turning out attention now to FIG. 2B, inhaler subassembly 6 is seen to include a pharmaceutical transfer assembly 104 mounted to a mouthpiece assembly 106, the combination secured to pressurized gas assembly 4.

Figure 2C:
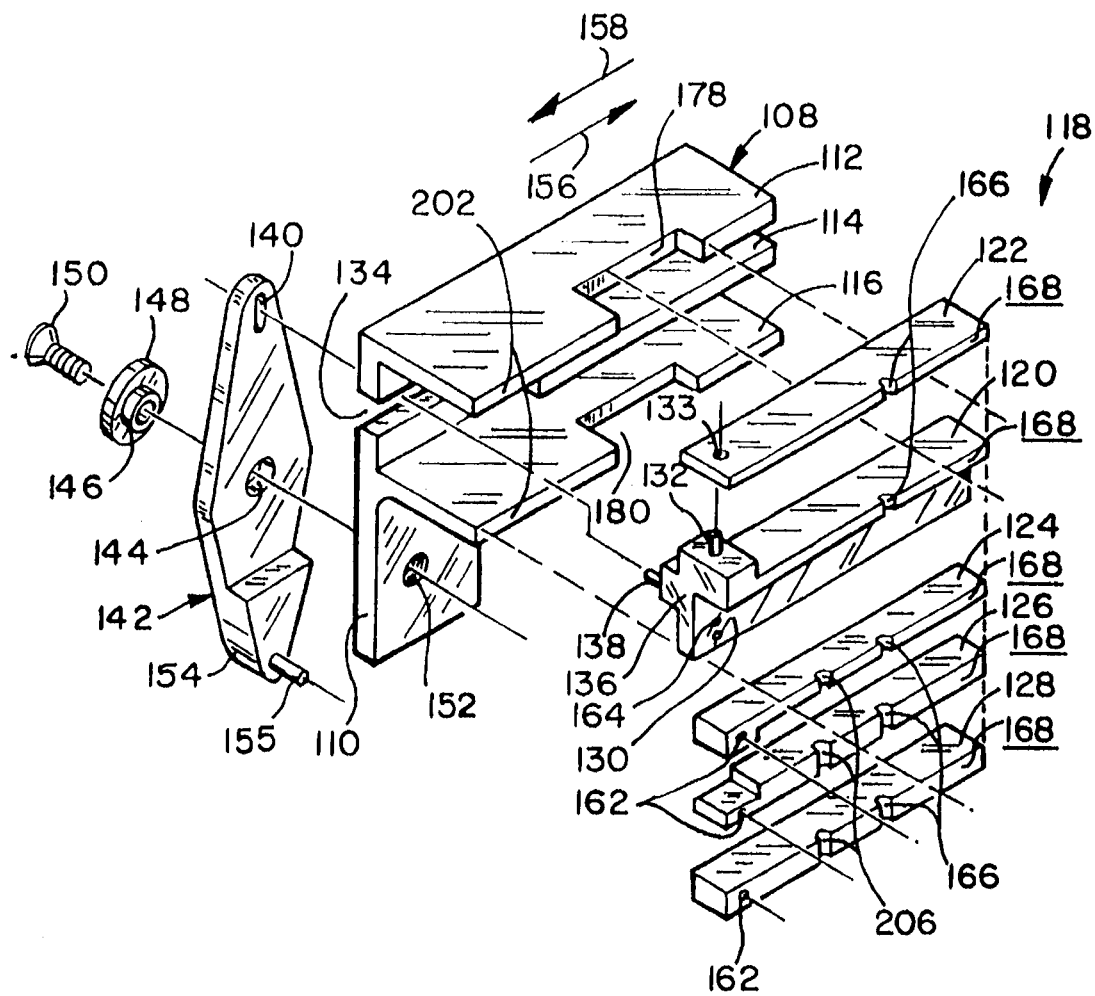
FIG. 2C is an enlarged view of a portion of the pharmaceutical transfer assembly of FIG. 2B.
Figure 2D:
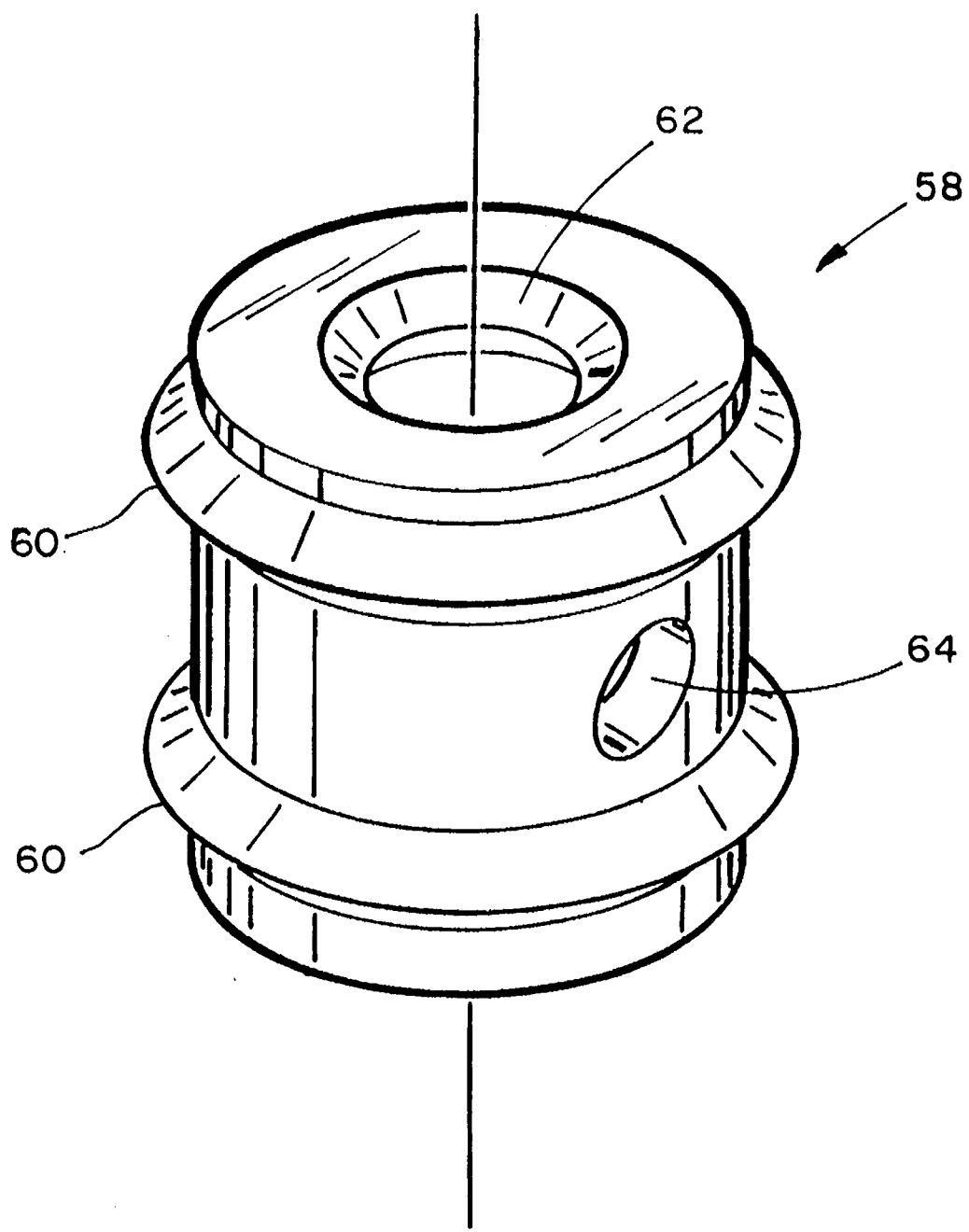
FIG. 2D is an enlarged view of the double lip seal of FIG. 2A.

Pharmaceutical transfer assembly 104 includes a dosing block 108 having a base 110 and three partitions 112, 114, 116 extending transversely from base 110. See FIG. 2C. A dosing plate assembly 118 includes a drive dosing plate 120 situated between partitions 114, 116, a set dosing plate 122 situated between partitions 112, 114 and three selectable dosing plates 124, 126, 128 mounted between partitions 114, 116 and resting on an extension 130 of drive dosing plate 120. Set dosing plate 122 is pinned to drive dosing plate 120 by the engagement of a pin 132 extending from drive dosing plate 120 within a hole 133 formed in set dosing plate 122. This is possible because partition 114 is shorter than partitions 112, 116.

Base 110 has a slot 134 formed in it within which a lug 136 extending from drive dosing plate 120 is housed. Lug 136 has a pin 138 extending therefrom which engages a slot 140 formed at one end of a lever arm 142. Lever arm 142 includes a central bore 144 within which the smaller diameter portion 146 of an axle washer 148 is housed. A screw 150 passes through axle washer 148 and into a threaded hole 152 in base 110. The opposite end 154 of lever arm 142 includes a cam pin 155 which rides within cam slot 102 formed in cam plate 94. See FIG. 2F. Thus, movement of stem handle sleeve 28 in proximal direction 72 until latch 44 engages surface 42 causes lever arm 142 to pivot about bore 144 thus driving drive and set dosing plates 120, 122 in first and second lateral directions 156, 158.

Selectable dosing plates 124–128 move with drive dosing plate 122 when dosing plates 124–128 are secured to extension 130 of drive dosing plate 120 by set screws 160. Set screws 160, shown in FIGS. 2B and 3, engage threaded holes 162 in dosing plates 124–128 and extend into holes 164 formed in extension 130 of drive dosing plate 120. The lateral or transverse movement of dosing plate assembly 118 is used to first fill pharmaceutical receptacles 166 formed in a set of coplanar surfaces 168 of dosing plates 120–128. This occurs during the transverse movement in the first lateral direction 156. Movement of dosing plate assembly 118 back in second lateral direction 158 causes pharmaceutical receptables 166, now containing the proper dose of pharmaceutical, to be aligned with an air flow path as will be described below.

Pharmaceutical transfer assembly 104 also includes a pharmaceutical reservoir block 170 (see FIG. 2B) including first and second pharmaceutical reservoirs 172, 174, containing first and second powdered pharmaceuticals 173, 175 respectively. See FIGS. 3 and 5. Reservoirs 172, 174 both have open tops and bottoms. Block 170 also includes a closed-bottom desiccant reservoir 176 containing a desiccant 177. A portion 181 of block 170 is mounted within two cut-outs 178, 180 formed in partitions 112, 114. Block 170 is secured to partitions 112, 116, such as with an adhesive. A resilient gasket 182 is captured between block 170 and dosing block 108 and provides a good seal with surfaces 168 of dosing plates 120–128. Also mounted within cut-outs 178, 180 is a view lens 184 aligned with and partially defining flow path 188. Lens 184 has a recess 190 which partially defines flow path 188. Recess 190 overlies pharmaceutical receptacles 166 when dosing plate assembly 118 is in the use position of FIGS. 1 and 3. Recess 190 and receptacle 166 become aligned with one another and define an entrainment region along flow path 188.

Dosing plate assembly 118 is preferably made from a plastic of a color which contrasts with the color of the pharmaceutical being dispensed. Typically, dosing plate assembly 118 is made of a black plastic to provide a strong contrast with the light colored pharmaceuticals which are often used. This makes viewing of the pharmaceutical 173, 175 within pharmaceutical receptacles 166 much easier.

Movement of dosing plate assembly 118 in first lateral direction 156 to a pharmaceutical pickup position causes pharmaceutical receptacle 166 formed in set dosing plate 122 to become aligned with first pharmaceutical reservoir 172 while the remaining pharmaceutical receptacles 166 become aligned with second pharmaceutical receptacle 174. Accordingly, two different powdered pharmaceuticals 173, 175 contained within receptacles 172, 174 can be dispensed in a single application using inhaler 2.

Figure 2E:
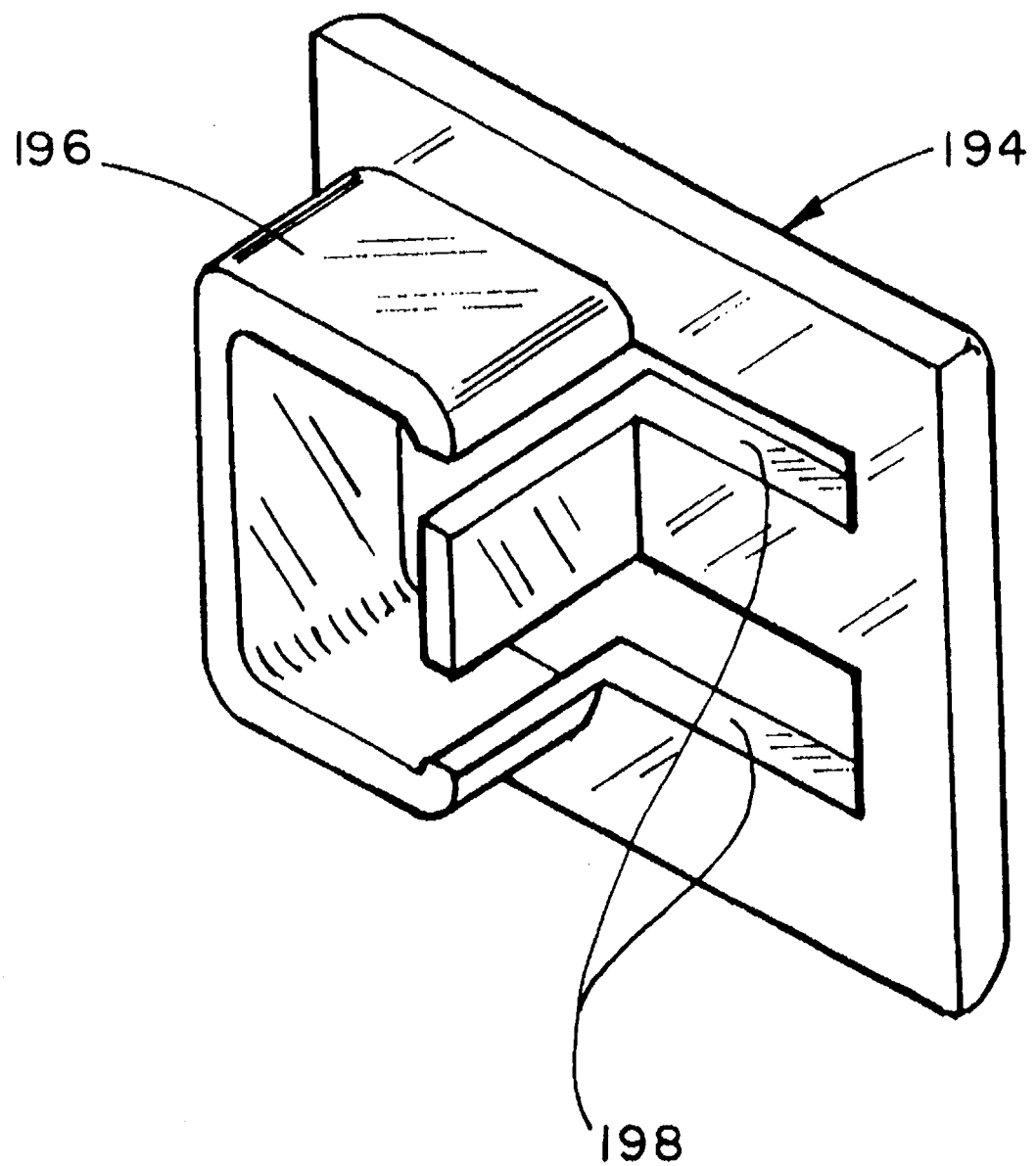
FIG. 2E is an enlarged view of the inner surface of the cap of FIG. 2B.
Figure 2F:
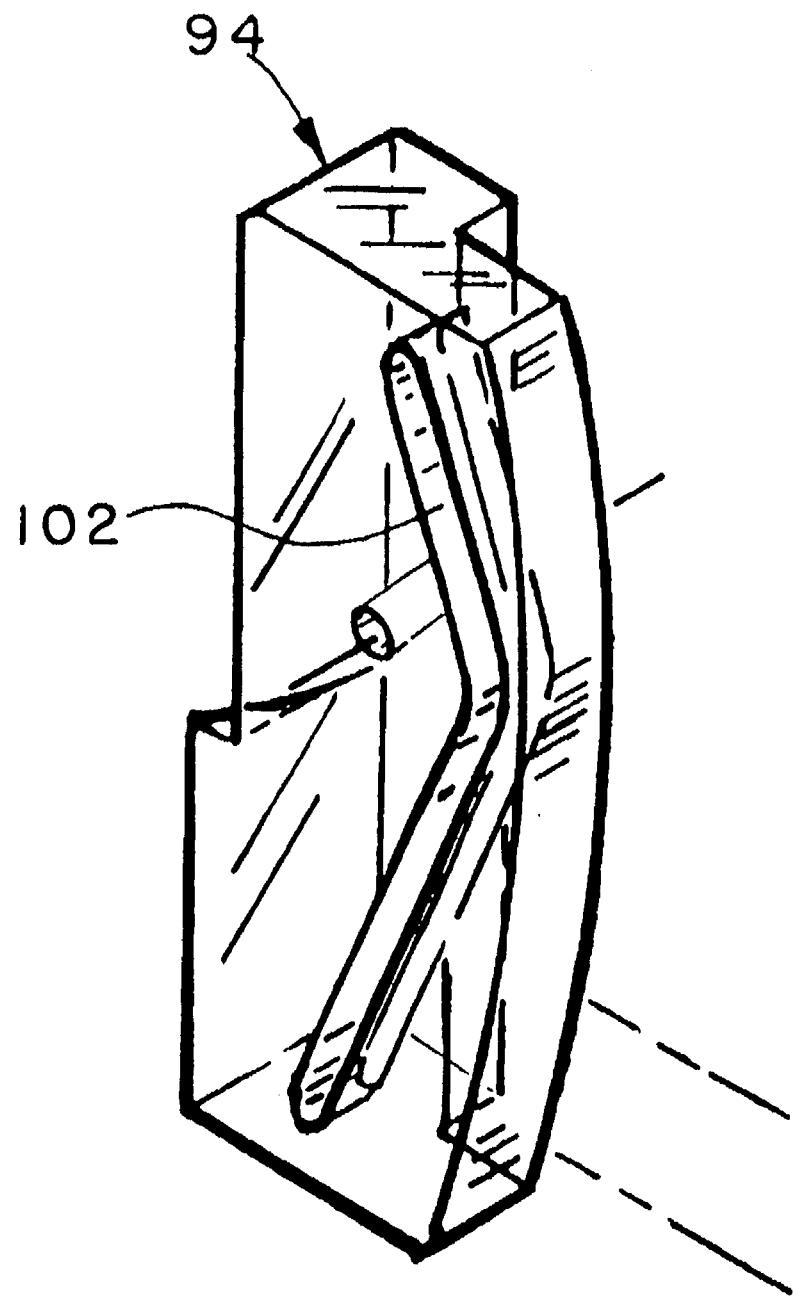
FIG. 2F illustrates the cam slot formed in the cam plate of FIG. 2A.

An air permeable membrane 192 is positioned above first and second pharmaceutical reservoirs 172, 174 and is captured between reservoir block 170 and a reservoir block cap 194. Cap 194 has an extension 196 see FIGS. 2E and 3, which fits within desiccant reservoir 176. Cap 194 has a pair of grooves or pathways 198 which permits air travel between desiccant reservoir 176 and pharmaceutical reservoirs 172, 174. In this way pharmaceuticals 173, 175 within reservoirs 172, 174 are kept dry by the provision of desiccant 177 within desiccant reservoir 176 and separated by membrane 192.

A retaining plate 200 is mounted to upper edges 202 of partitions 112, 116 to overlie dosing plate assembly 118. Retaining plate 200 includes 3 holes 204 through which set screws 160 can be accessed and can pass. That is, by backing set screws 160 out of holes 164 and into holes 204, one or more of selectable dosing plates 124, 126, 128 become locked to retaining plate 200 and thus to dosing block 108. Therefore, pivotal movement of lever arm 142 through the actuation of stem handle sleeve 28 leaves selectable dosing plates 124–128 in the pharmaceutical pickup position, suggested by the dashed lines in FIG. 3, with pharmaceutical receptacles 166 underlying second pharmaceutical reservoir 174. In this situation, so as not to block flow path 188 when one or more of selectable dosing plates 124–128 are not being used to carry second pharmaceutical 174 into the entrainment region of the flow path, plates 124–128 each have a dummy pharmaceutical receptacle 206 which will underlie lens 190 and thus partially define flow path 188 when dosing plate assembly 118 is in the use position of FIGS. 1 and 3 after being moved in second lateral direction 158.

Mouthpiece assembly 106 includes a bypass channel 208 having a central cutout region 210, a pair of side walls 212 and a pair of end walls 214. Each sidewall 212 has a rectangular cutout 216 sized to mate with that portion of base 110 of dosing block 108 aligned with flow path 188. Side walls 212 and end walls 214 define distal and proximal sealing surfaces 218, 220. Sealing surface 218 engages the outer surface of member 14 in a manner to position passage 70 within cutout region 210. Mouthpiece assembly 106 also includes a mouthpiece mount 22 which is generally cylindrical but has a cutout 224 at its distal end. Proximal sealing surface 220 engages mouthpiece mount 222 at a position proximal of cutout 224 so that the interior of mouthpiece mount 222 is fluidly coupled to cutout region 210 of bypass channel 208 through cutout 224.

A plume diffuser 226 is mounted within mouthpiece mount 222. Diffuser 226 has a conical opening 228 extending along its length. Conical opening 228 is larger at its proximal end 230 than at its distal end 232. Conical opening 228 acts as a diffuser to slow down or retard the movement of air and entrained pharmeaceutical 173, 175 moving through the diffuser along flow path 188. Diffuser 226 also includes a D-shaped based 233 by which air can pass from the interior of mouthpiece mount 222 to a region surrounding the proximal end 230 of conical opening 228. Finally, a mouthpiece 234 is secured within mouthpiece mount 222 and retains a plume diffuser 226 in place within mouthpiece mount 222.

Most of the components of inhaler 2 are made of a biocompatible plastic such as polycarbonate. Plume diffuser 226, can plate 94 and lens 184 are all clear, preferably made of acrylic. The screws, boost air tube 54 and reset wire form 86 are preferably stainless steel while o-rings 22, 50 and gasket 182 are preferably an elastomeric material, such as silicone rubber.

In use, the user first determines the amounts and proportions of the first and second pharmaceuticals 173, 175 held within first and second pharmaceutical reservoirs 172, 174 which are to be dispensed. With dosing plates assembly 118 moved in second lateral direction 158 to the use position, set screws 160 are adjusted as needed to secure selectable dosing plates 124–128 to either drive dosing plate 120 or retaining plate 200. In the preferred embodiment drive dosing plate 120 and set dosing plate 122 are always used so that a mixture of the first and second pharmaceuticals are, with this embodiment, generally present during use. However, other configurations and arrangements could be used as well. In addition, it is evident that since selectable dosing plate 124 is narrower than selectable dosing plates 126, 128, a rather extensive range of amounts and proportions of pharmaceuticals can be dispensed using the present invention.

At the end of the stroke of plunger 16, see FIG. 1, air is compressed within cylinder 8 between piston 20 and barrel plug 48. The user now inhales on mouthpiece 234 which causes ambient air to enter inlets 68, move past breath trigger disk 73 and through passage 70. This causes two things to happen. First ambient air continues along cutout region 210 of bypass channel 208, into mouthpiece mount 222, between plume diffuser 226 and mouthpiece 234 for inhalation by the user. Second, breath trigger disk 73 moves in proximal direction 72 thus moving boost air tube 54 therewith. This movement causes distal end 80 of tube 54 to become fluidly connected to the interior of double-lip seal 58 and thus to the compressed air within cylinder 8 captured between piston 20 and barrel plug 48 by virtue of radial bore 64 formed in double-lip seal 58 and vent hole 82 formed in barrel plug 48. This pressurized air then rushes through boost air tube 54, along the entrainment region of the flow path 188 between pharmaceutical receptacles 166 (and in some cases dummy pharmaceutical receptacles 206) and recess 190 formed in lens 186, through proximal end 232 of conical opening 228, through the outwardly expanding conical opening, and through mouthpiece 234 for inhalation by the user.

To repeat the process, the user presses on finger lever 38, which moves catch 44 away from surface 42, grasps distal end 26 of stem handle sleeve 28, pulls sleeve 28 in distal direction 46 and releases finger lever 38. Air is pulled into cylinder 8 through tube 54 over most of this distal movement. At the end of that stroke, the user forces sleeve 28 in proximal direction 72 thus compressing the air in cylinder 8 until catch 44 is repositioned opposite surface 42. During the cycling of sleeve 28, arm 142 pivots to refill pharmaceutical receptacles 166.

Figure 4:
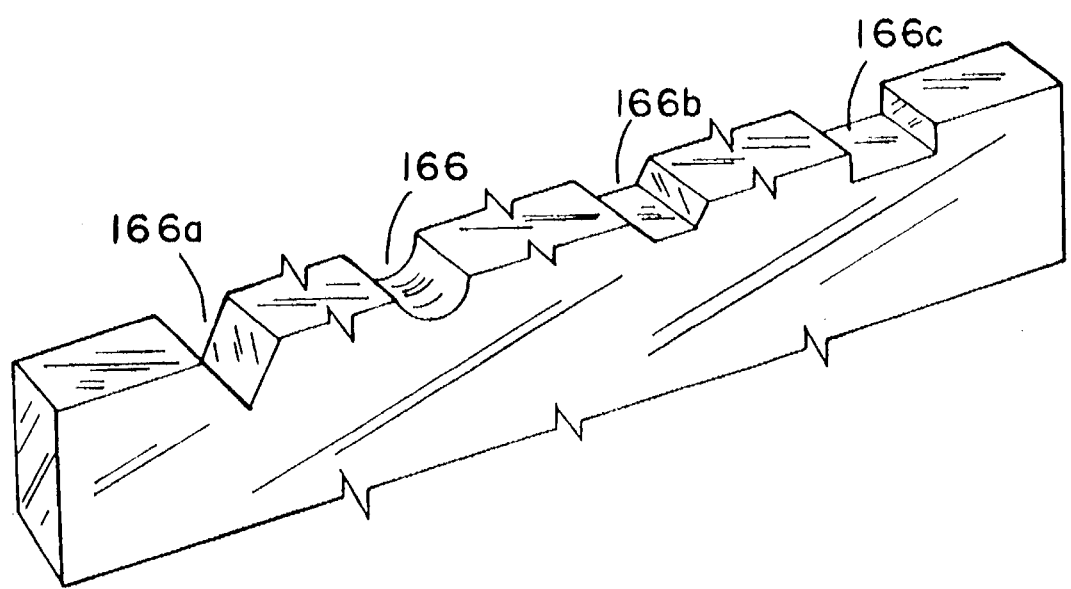
FIG. 4 illustrates three alternative pharmaceutical receptacle shapes.

FIG. 4 illustrates four different shaped pharmaceutical receptacles. The shape, size and configuration of the pharmaceutical receptacles are determined by the size of the pharmaceutical particles and their affinity for the material from which dosing plate assembly 118 is made. For example, some finely divided pharmaceuticals are susceptible to packing and thus the V-shaped receptacle 166a may not be the best configuration. Pharmaceutical receptacles are typically only about 0.5 mm wide, 1.0 to 5.0 mm long and 0.25 to 0.50 mm deep. The quantities are quite small so that, it has been found, that gravity is less of a factor than surface adhesion characteristics. Shapes other than the triangular shape of receptacle 166a, the parabolic/hyperbolic shape of receptacle 166, the trapezoidal shape of receptacle 166b or the rectangular shape of receptacle 166c can be used as well.

Figure 5:
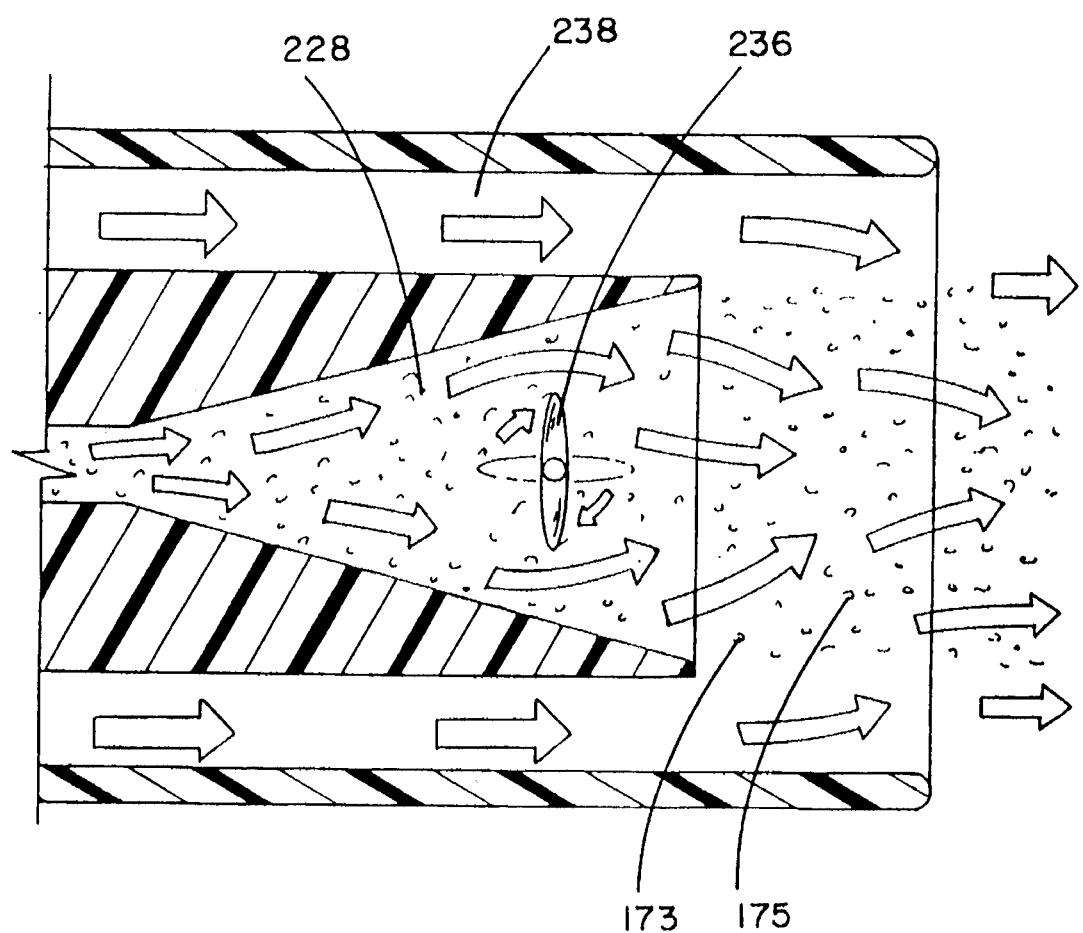
FIG. 5 is a simplified view of a portion of an alternative embodiment of the mouthpiece assembly of FIG. 2B with an adjustable deflector along the flow path.

It has been found that certain pharmaceuticals which are difficult to be entrained must be entrained using a higher velocity air stream along the flow path. However, it has also been found that such a high velocity air pulse can cause many individuals to gag or cough, even with the use of the diffuser 226. Accordingly, it may be desired to use an adjustable deflector 236 as shown in FIG. 5. Adjustable deflector 236 would typically be used within conical opening 228 of the plume diffuser to help soften the air pulse thereby reducing the pulsed air speed and slowing the central flow of air and pharmaceutical mixture to be closer to that of the lower velocity ambient air stream 238 circumscribing the air stream along the main flow path 188.

Figures 6A, 6B:
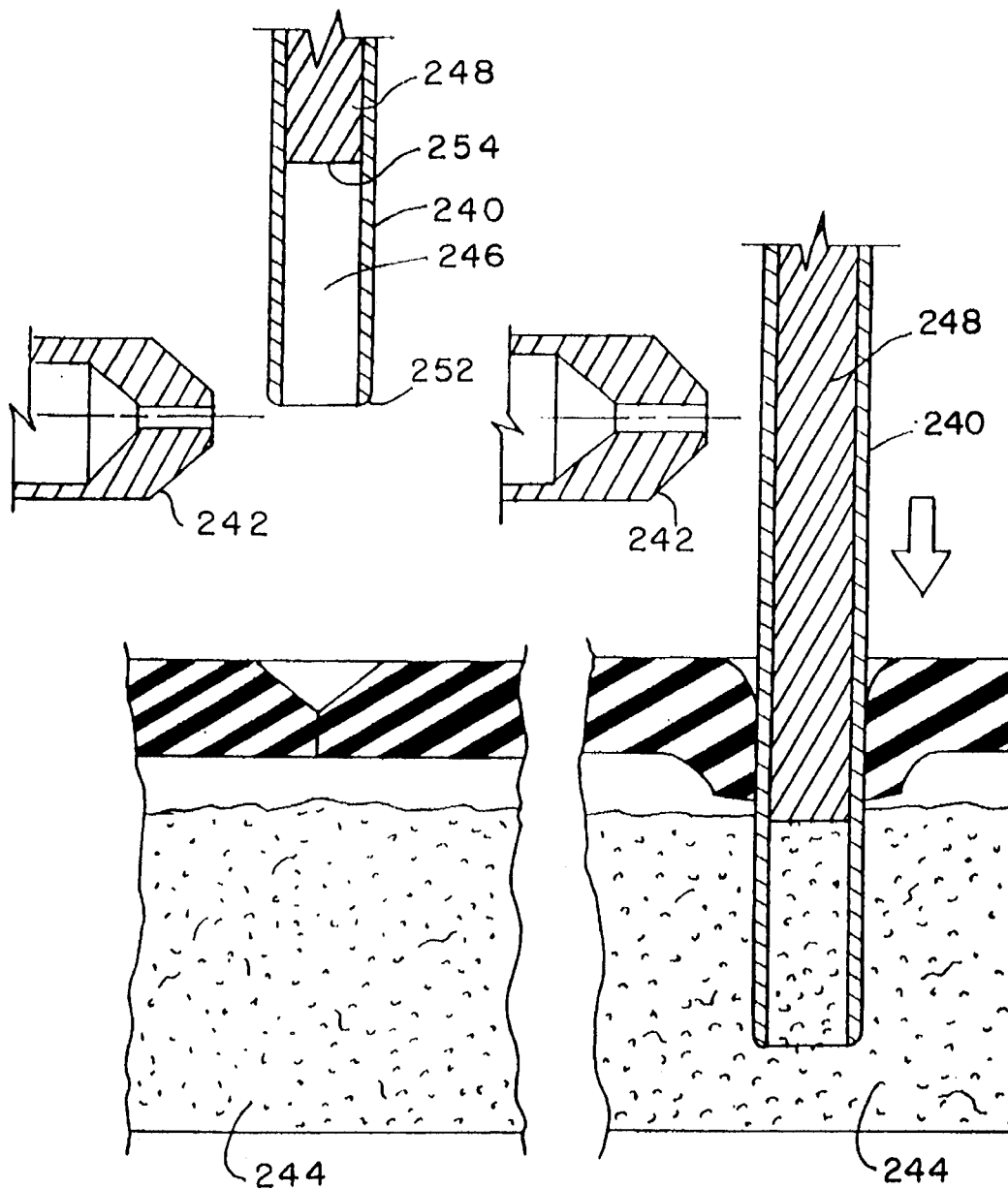
FIGS. 6A–6C are simplified, schematic representations illustrating the main working components of an alternative embodiment of the pharmaceutical transfer assembly of FIG. 2B.
Figure 6C:
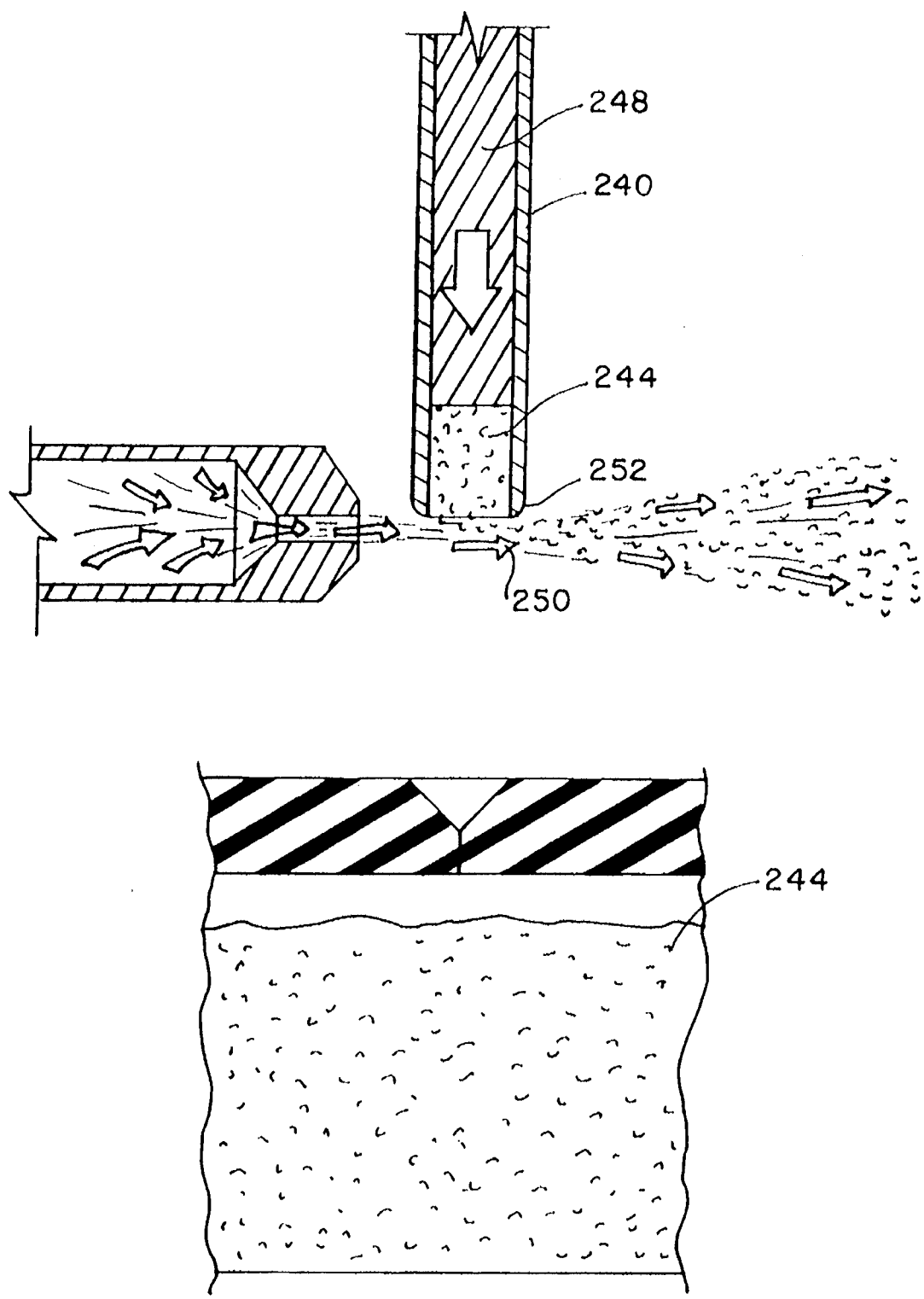

FIGS. 6A–6C illustrate, in simplified form, an alternative embodiment of the invention which uses a different mechanism for transferring a quantity of a pharmaceutical from a pharmaceutical reservoir to an entrainment position along the flow path. In FIG. 6A transfer tube 240 is shown adjacent a nozzle 242 and above a pharmaceutical reservoir 244. Transfer tube 240 moves from the position of FIG. 6A to the pharmaceutical pickup position of FIG. 6B at which point the powdered pharmaceutical 244 enters the hollow interior 246 of transfer tube 240. FIG. 6C illustrates the return of transfer tube 240 to the use position, the timed expulsion of powdered pharmaceutical 244 from transfer tube 240 by an internal piston 248 which occurs as an airstream 250 if directed past the tip 252 of transfer tube 240. In appropriate circumstances the invention can also be used with liquid pharmaceuticals as well. If getting powdered pharmaceutical 244 into hollow interior 246 is a problem, it may be desired to position the end 254 of internal piston 248 adjacent tip 252 of transfer tube 240 prior to moving from the use position of FIG. 6A to the pharmaceutical pickup position of FIG. 6B. As tip 252 begins to enter the reservoir of powdered pharmaceutical 244, the internal piston can then be withdrawn back up into transfer tube 240 thus creating a partial vacuum within the interior of transfer tube 240 helping to pull powdered pharmaceutical 244 up into hollow interior 246 of transfer tube 240.

Figure 7:
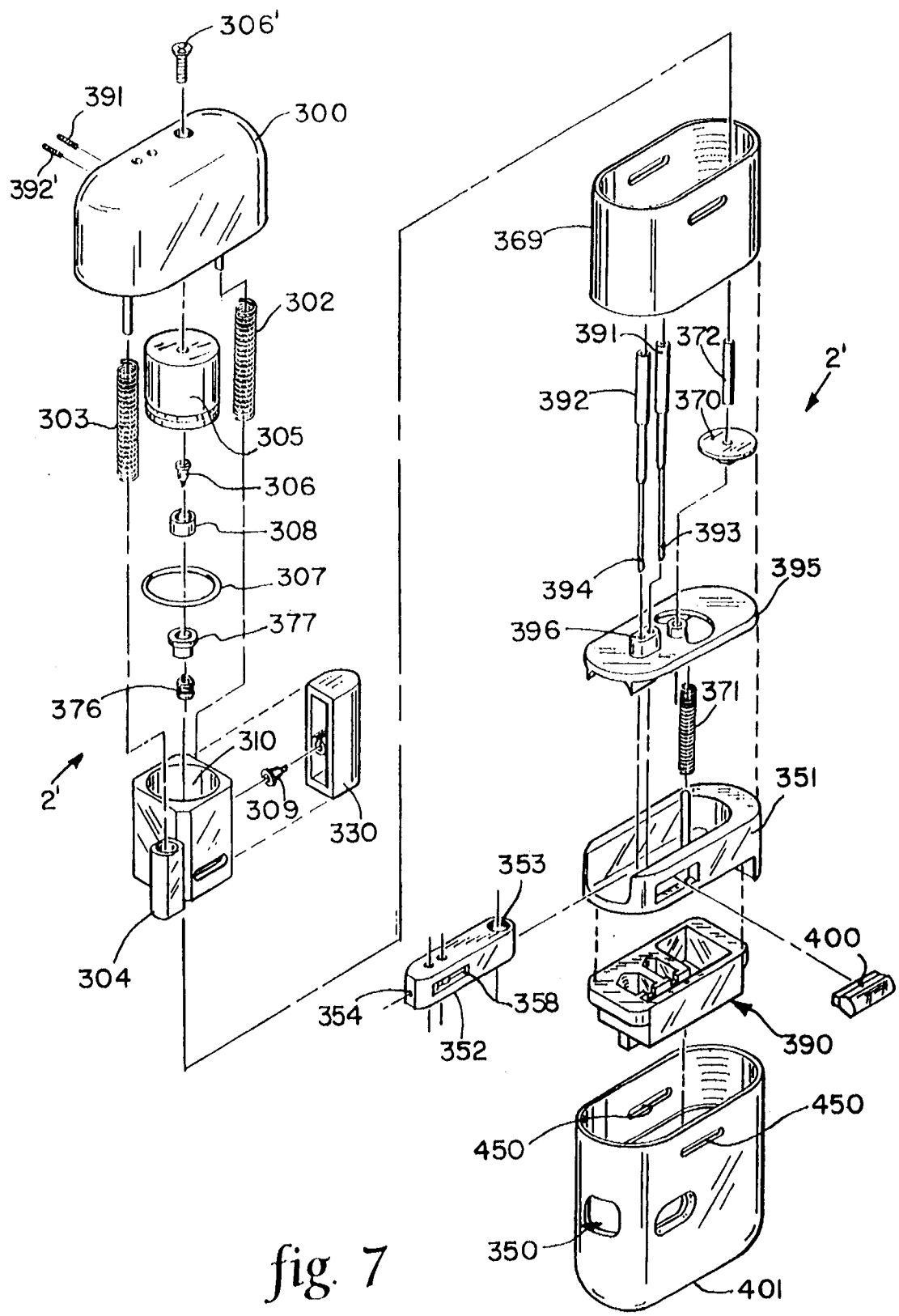
FIG. 7 is an exploded view of the streamlined configuration of the device which incorporates into a pocket size rounded case the functions of the dispenser of FIGS. 1–6C.
Figure 8:
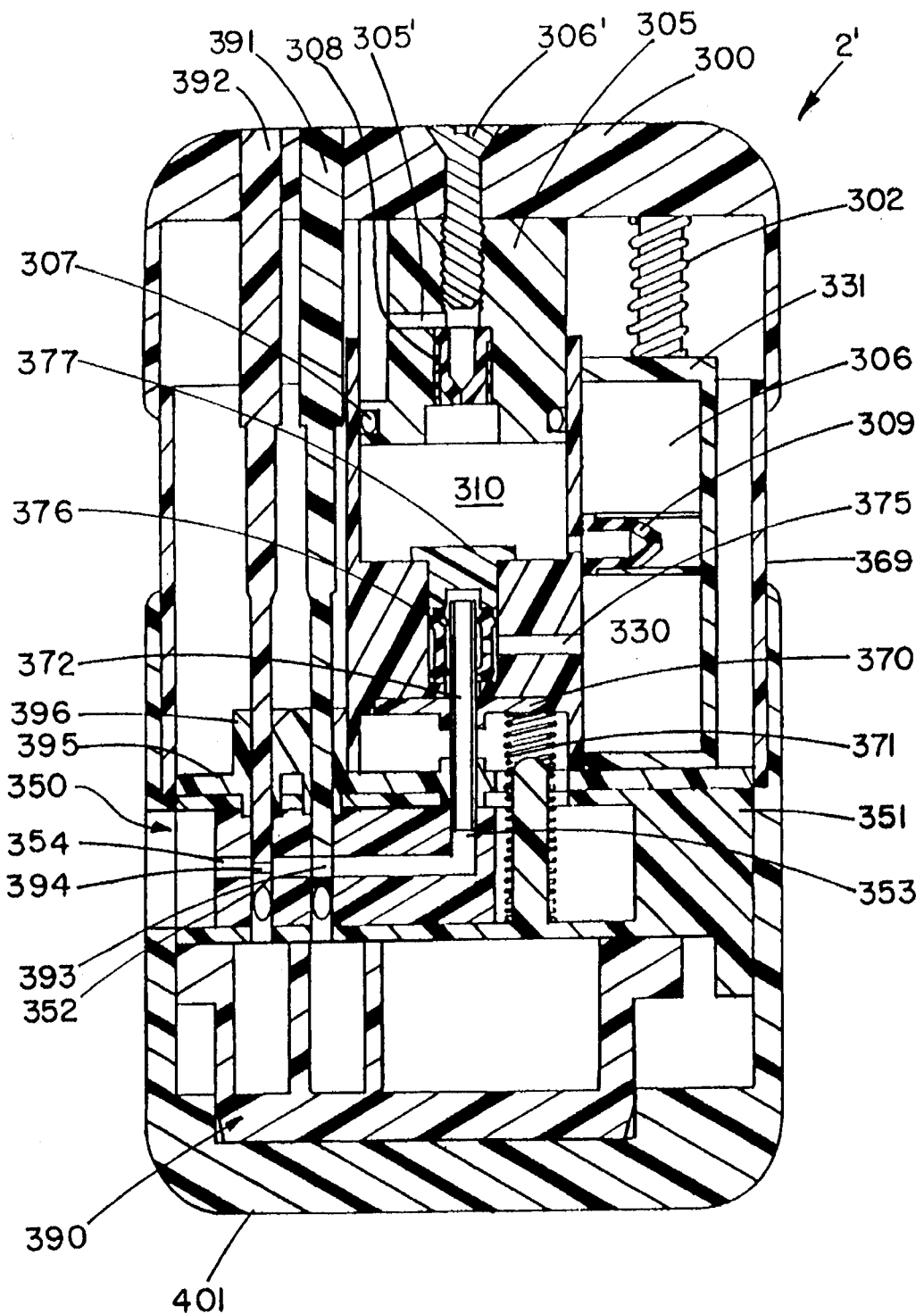
FIG. 8 is a side elevation section of the assembled device of FIG. 7 from which the operation of the device can be conveniently understood; and, FIG. 9A and 9B are respective details of the medicant bearing chambers providing tapered bottoms for assured filling of the dose rods and a side elevation of the dose rod illustrating the pocket for metering medicant powder upon penetration into and out of the medicant chambers.

Referring simultaneously to FIGS. 7 and 8—and with temporarily greater attention to FIG. 8—the operating characteristics of a compact, pocket sized inhaler 2' of this invention can be set forth.

Referring to FIG. 8, a central section has been taken through the compact device along a plane taken half way through the device. Interestingly, this is the same horizontal plane in which the disperser is held during use—that is the dispenser would be parallel to ground and horizontally normal to both gravity and the spine of a standing user. In understanding this embodiment, operation will be described first with assembly set forth second.

Referring to FIG. 8, the dispenser includes respective activation cap 300 and medication reservoir cap 401. To activate the dispenser, these two ends are compressed—one towards the other. Full compression accomplishes two functions. First, an accumulated air charge is acquired in chamber 330. Secondly, the respective dose rods 391, 392 enter into medication reservoirs 390 and pick up the prescribed portions of powdered medication.

Accumulation of the charge of air is easy to understand. Piston 305 acts to compress air in chamber 310. Air enters chamber 310 through check valve 306 and exits through check valve 309 into chamber 330. Since no air escape path is normally open, the compressed air is maintained in chamber 330.

Action of the dose rods 391, 392 to accumulate the prescribed dosage at compartments 393, 394 is likewise easy to understand. Specifically, dose rods 391, 392 at respective compartments 393, 394 move out of registration with entrainment passageway 354 and into the interior of medication reservoirs 390. Interior of each reservoir 390A, 390B, dose rods accumulate the prescribed dose from the tapered bottom 460 of the respective reservoirs. For example, and referring to FIGS. 9A and 9B, it can be seen that medicant chambers 390A and 390B have tapered bottoms 460. Medicant powder is maintained in a dry condition interior of these chambers by a desiccant chamber 462 maintaining a substantially water free environment through water permeable membrane or screen 461. Upon insertion to the chambers 390A and 390B, filling of dosage compartments 393 (and 394—not shown in FIGS. 9A and 9B) occurs.

On release of compression between activation cap 300 and medication reservoir cap 401, compressed air is stored in reservoir 330 and the respective dose rods 391, 392 registered at dose compartments 393, 394 to air passage 354 in the vicinity of outlet 350. At this juncture, the user may inspect the respective dosage compartments 393, 394 through clear lens 400 to assure that these compartments are filled with the prescribed and measured dose.

Dispensing is activated by the user sucking on outlet 350. A vacuum is drawn on disc 370 overcoming the bias of spring 371. Disc 370 lifts exposing tube 372 in between seals 376. Compressed air from chamber 330 passes down passageway 375, through tube 372, into entrainment passage 354 and by and through dose rods 391, 392 at respective dose compartments 393, 394 to entrain the powder medication into an air stream inhaled by the user. Complete flushing of the system is assured by providing a path for further inhalation including slots 450 (See FIG. 7) which communicate to entrainment air passage 354. Once inhalation of the prescribed dosages is complete, the user can observe dose rods 391, 392, at dose compartments 393, 394 through window 400 to assure complete evacuation of the portioned medicant powder.

Figures 9A, 9B:
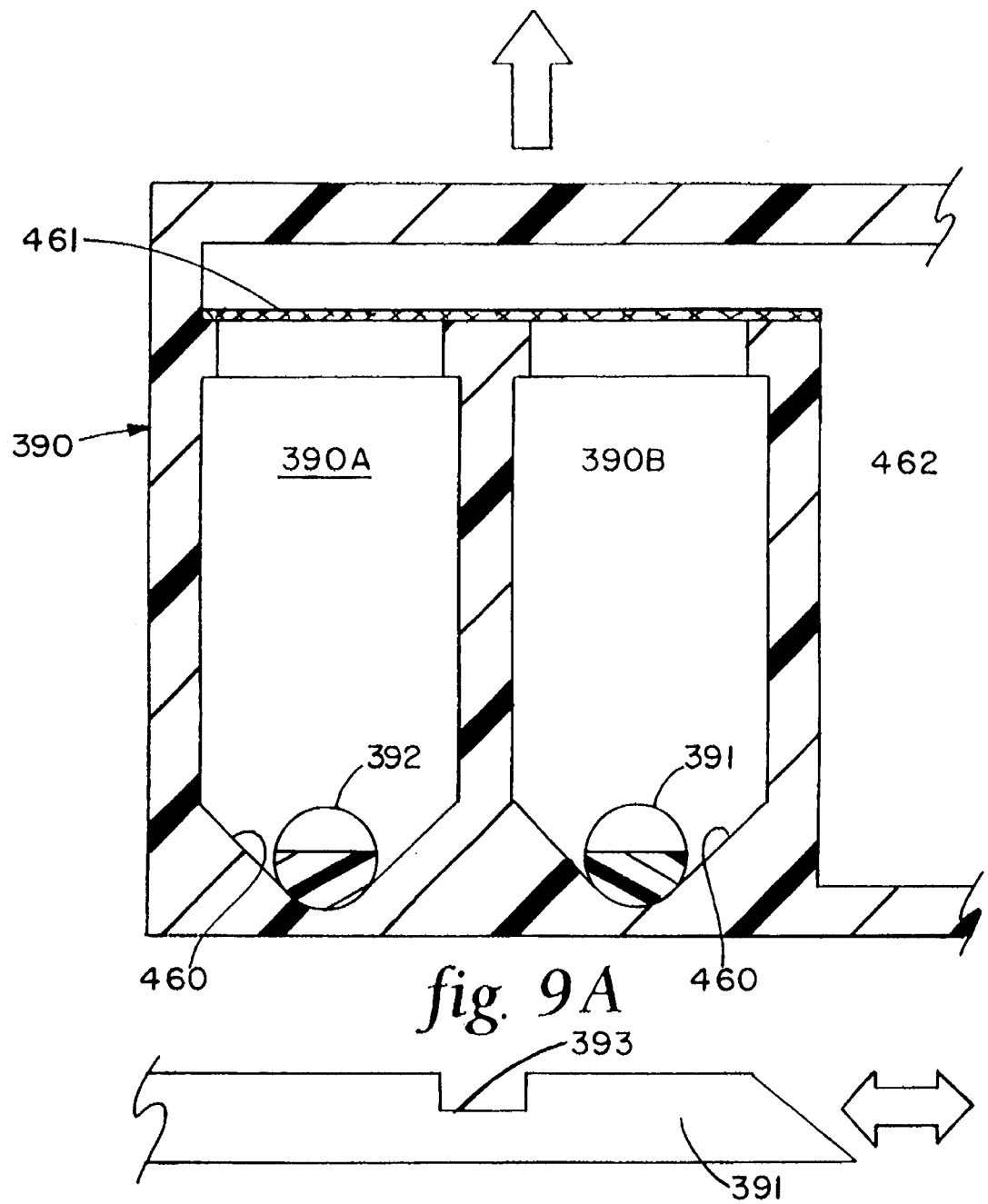

Having set forth the general operation, assembly can be understood with primary reference to FIG. 7 and secondary references to FIGS. 8, 9A and 9B.

Activation cap 300 bears against three active members. These members include shaft mounted springs 302, 303, on either side for symmetrical loading of the cap and central air compression piston 305. Springs 302, 303, bear on spring receiving members 304 (shown only in FIG. 7). When springs 302, 303 are compressed through compression of activation cap 300 toward medication reservoir cap 401, cylinder 305 compresses air in chamber 310 with sliding passage of seal 307 along chamber 310 and simultaneous discharge through check valve 309 into storage chamber 330. When caps 300, 401 are released, check valve 306 in valve seat 308 admits a new charge of air through the central portion of cylinder 305 and communicated channel 305'.

Activation cap 300 includes screws 305' for fastening piston 305, and respective screws 391', 392' for maintaining dose rods 391, 392 in place. As should be apparent, dose rods can be changed so that the respective compartments 393, 394 meter the prescribed amount. For example, in the section of FIG. 8, it can clearly be seen that compartment 393 exceeds in size compartment 394.

Activation cap 300 slides on inside walls over the surface of middle member 369. It is end limited in its travel by conventional end limit mechanisms—not shown—so that the respective caps 300, 401 do not separate. Middle member 369 fastens to chamber to 395 which includes gathering apertures 396 for dose rods 391, 392 and an underlying seat for disc valve 370. Additionally, medication cap 401 frictionally fastens over and adheres to mid member 369 in a friction fit.

Reciprocating tube 372 is mounted interiorly of disc 370. This disc is biased to the normally closed position by spring 371. Spring 371 fits against air passage base plate 351. Air passage base plate 351 defines and upwardly exposed U-sectioned slot which receives air passage plug 352 having air inlet 353 and air outlet 354. This plug includes a slot 358 which allows inspection of dose rods 391, 392 at compartments 393, 394 through an inserted magnifying clear lens 400.

Medicant chamber 390 fits immediately below air passage base plate 351 and within cap 401. This cap includes aperture 350 over which the user draws a vacuum for opening disc valve 370.

Returning to the section of FIG. 8, cap 401 is a friction fit over mid section 369 and is held securely in place. Medication can be resupplied by removing cap 401 against this friction fit, accessing screws (not shown) holding medicant chamber 390 to air passage base plate 351 and replacing the medicant chamber 390. In this way, medicant powder as well as dose rods 391, 392 can be altered to change both medication and prescription.

Other modifications and variation can be made to the disclosed embodiments without departing from the subject of the invention as defined in the following claims. For example, a greater or lesser number of dosing plates could be used with a greater or lesser number of different pharmaceuticals. The invention could also be used with different types of pressurized gas source assemblies 4. For example, a miniature electric pump could be used to create a surge of pressurized gas. A $CO_2$ cartridge type of pressurized gas source could be used. Also, in some cases entrainment of the pharmaceutical does not require a high pressure gas source. In such cases simple inhalation by the user can create sufficient air flow to entrain the pharmaceutical sufficiently. In these, as well as other, situations dual, coaxial air flows would likely not be needed. In addition, a counter could be mounted to inhaler 2 to count the number of cycles of sleeve 28 and plunger 16. Two or more pressurized gas sources could be used with a single inhaler. A series of surfaces 42 could be used to permit the pressure of the air pulse along flow path 188 to be varied.

What is claimed is:

1. A pharmaceutical inhaler comprising:

a gas source;

a main housing having an entrance and an exit and defining a gas flow path from the entrance to the exit, the gas flow path defining an entrainment region therealong, the entrance fluidly coupled to the gas source;

first and second reservoirs carried by the main housing;

first and second supplies of first and second powdered pharmaceuticals within the first and second reservoirs respectively;

a pharmaceutical transfer assembly including a plurality of dosing members each having a pharmaceutical receptacle, the dosing members being moveable between pharmaceutical pickup positions, at which a quantity of each of the first and second pharmaceuticals is transferred from the first and second reservoirs to the pharmaceutical receptacle, and use positions, at which the quantities of the pharmaceuticals are positioned at an entrainment region along the flow path;

a dosing member driver which moves selected ones of the dosing members between the pharmaceutical pickup positions and the use positions so to select the quantities of the pharmaceuticals positioned at the entrainment region of the flow path;

whereby a gas flowing along the gas flow path from the entrance to the exit entrains the quantity of pharmaceutical at the entrainment region so to deliver said quantity of pharmaceutical to a user through the exit; and the dosing members being moveable back to the pharmaceutical pickup positions and then back to the use positions at which a second quantity of the pharmaceutical is positioned at the entrainment region for subsequent entrainment by a second gas flow along the gas flow path.

2. The inhaler of claim 1 wherein the exit includes a mouthpiece.

3. The inhaler of claim 1 wherein the source of gas includes a source of uncompressd air.

4. The inhaler of claim 1 wherein the source of gas includes a source of compressed gas.

5. The inhaler of claim 4 wherein the source of compressed gas includes a piston and cylinder arrangement.

6. The inhaler of claim 4 further comprising a trigger assembly, including a user-actuated trigger, operably coupled to the source of compressed gas to permit a quantity of compressed gas to be directed along the gas flow path upon actuation of the trigger.

7. The inhaler of claim 6 wherein the trigger is an air flow actuated trigger.

8. The inhaler of claim 6 wherein the user-activated trigger includes a trigger disc movable between a first position, at which the gas source is fluidly coupled to the entrainment region, and a second position, at which the gas source is fluidly isolated from the entrainment region, the trigger disc being movable from the second position to the first position upon inhalation at the exit by a user.

9. The inhaler of claim 1 wherein the pharmaceutical receptacle is defined by an opening formed in a surface of the dosing member.

10. The inhaler of claim 9 wherein the dosing member is an elongate member.

11. The inhaler of claim 9 wherein the surface of the dosing member is an upper surface.

12. The inhaler of claim 11 wherein a reservoir overlies the dosing member, the reservoir having an open bottom which overlies the pharmaceutical receptacle when the dosing member is at the pharmaceutical pickup position.

13. The inhaler of claim 1 wherein the dosing member driver includes a main driver and means for selectively coupling said selected ones of the dosing members to the main driver.

14. The inhaler of claim 13 wherein the selectively coupling means includes pins threadably mounted to at least the selected ones of the dosing members, the pins being manipulatable to engagement with either of the main driver or the main housing.

15. The inhaler of claim 1 further comprising a diffuser positioned along the flow path between the entrainment region and the exit, the diffuser configured to slow fluid flow of gas and entrained pharmaceutical.

16. The inhaler of claim 1 further comprising a secondary gas flow path completely circumscribing the flow path along at least a part of a length of the flow path, the secondary gas flow path extending between the exit and a secondary entrance.

17. The inhaler of claim 16 wherein including a secondary entrance opening into the ambient environment.

18. The inhaler of claim 1 further comprising a view port, carried by the main housing, for viewing a pharmaceutical receptacle of the dosing member with pharmaceutical therein.

19. The inhaler of claim 18 wherein the view port includes a magnifying lens element.

20. The inhaler of claim 18 wherein the view port is situated at the entrainment region of the flow path.

21. The inhaler of claim 18 wherein the dosing member is of a color which contrasts with the color of the pharmaceutical to aid viewing the quantity of the pharmaceutical.

22. A pharmaceutical inhaler comprising:

a pressurized gas source;

a main housing having an entrance and an exit and defining a gas flow path from the entrance to the exit, the entrance fluidly coupled to the pressurized gas source;

first and second reservoirs carried by the main housing;

first and second supplies of first and second pharmaceuticals within the first and second reservoirs respectively;

a pharmaceutical transfer assembly including a plurality of dosing members each having a pharmaceutical receptacle, the dosing members being moveable between pharmaceutical pickup positions, at which a quantity of each of the first and second pharmaceuticals is transferred from the first and second reservoirs to the pharmaceutical receptacles, and a use position, at which the quantities of the pharmaceuticals are positioned at an entrainment region along the flow path;

a dosing member drive which moves selected ones of the dosing members between the pharmaceutical pickup positions and the use positions so to select the quantity of the pharmaceuticals positioned at the entrainment region of the flow path;

a secondary gas flow path circumscribing the flow path along at least a part of the length of the flow path, the secondary gas flow path extending between the exit and a secondary entrance opening to the ambient atmosphere;

a view port, carried by the main housing, for viewing the pharmaceutical receptacles of the dosing member at the entrainment region;

whereby a gas flowing along the gas flow path from the entrance to the exit entrains the quantities of pharmaceutical at the entrainment region so to deliver said quantities of pharmaceutical to a user through the exit; and the dosing members being moveable back to the pharmaceutical pickup positions and then back to the use positions at which second quantities of the pharmaceuticals are positioned at the entrainment region for subsequent entrainment by a second gas flow along the gas flow path.

23. A method for inhaling a dose of first and second powdered pharmaceuticals comprising the following steps:

providing an inhaler with first and second supplies of the first and second powdered pharmaceuticals, each said supply sufficient for a plurality of said doses;

removing first and second quantities of the first and second pharmaceuticals from the first and second supplies of the first and second pharmaceuticals, respectively;

positioning the first and second quantities at an entrainment region along a gas flow path within the inhaler;

generating a gas flow along the gas flow path;

entraining the first and second quantities within the gas flow; and inhaling the first and second quantities of the pharmaceuticals entrained in the gas flow.

24. The method of claim 23 further comprising the step of viewing at least one of said first and second quantities prior to the entraining step.

25. The method of claim 24 wherein the viewing step is carried out by viewing at least one of said first and second quantities on a contrasting color background.

26. The method of claim 23 further comprising the step of providing a secondary flow path substantially completely surrounding at least a portion of the gas flow path.

27. The method of claim 23 further comprising the step of lowering a speed of the gas flow and entrained pharmaceutical prior to inhaling the chosen quantity.

28. A method for inhaling a dose of a pharmaceutical comprising the following steps:

providing an inhaler with a gas flow path and first and second supplies of first and second pharmaceuticals, said supplies each sufficient for a plurality of said doses;

providing a secondary flow path substantially completely surrounding at least a portion of the gas flow path;

removing chosen quantities of the first and second pharmaceuticals from said supplies;

positioning the chosen quantities at an entrainment region along a gas flow path within the inhaler;

viewing the chosen quantities;

entraining the chosen quantities within a gas flow;

lowering a speed of the gas flow and entrained pharmaceuticals prior to the inhaling step; and inhaling the chosen quantities of the pharmaceutical entrained in the gas flow.

* * * * *